United States Patent [19]

Weuthen et al.

[11] Patent Number: 5,480,979
[45] Date of Patent: Jan. 2, 1996

[54] PROCESS FOR THE PRODUCTION OF ALKYL AND/OR ALKENYL OLIGOGLYCOSIDES

[75] Inventors: Manfred Weuthen, Solingen; Karlheinz Hill, Erkrath; Paul Schulz, Wuppertal, all of Germany

[73] Assignee: Henkel Kommanditgesellschaft auf Aktien, Duesseldorf, Germany

[21] Appl. No.: 244,053

[22] PCT Filed: Nov. 6, 1992

[86] PCT No.: PCT/EP92/02552

§ 371 Date: May 13, 1994

§ 102(e) Date: May 13, 1994

[87] PCT Pub. No.: WO93/10132

PCT Pub. Date: May 27, 1993

[30] Foreign Application Priority Data

Nov. 15, 1991 [DE] Germany .......................... 41 37 636.6

[51] Int. Cl.⁶ .......................... C07H 15/04; C07H 15/08; C07H 1/00
[52] U.S. Cl. .......................... 536/18.6; 536/4.1; 536/18.5
[58] Field of Search ................... 536/18.6, 18.5, 536/4.1

[56] References Cited

U.S. PATENT DOCUMENTS 3,974,138  8/1976  Lew ......................... 536/4.1

5,003,057  3/1991  McCurry et al. ................. 536/18.6

FOREIGN PATENT DOCUMENTS

| 0538363 | 8/1984 | Australia . |
| 0301298 | 2/1989 | European Pat. Off. . |
| 0319616 | 6/1989 | European Pat. Off. . |
| 0415192 | 3/1991 | European Pat. Off. . |
| 9003977 | 4/1990 | WIPO . |

OTHER PUBLICATIONS

D. S. Kemp et al, "Organic Chemistry" published 1980 by Worth Publishers, Inc. (New York, N.Y.), pp. 285–314.

Chemical Abstracts; vol. 91, No. 19, Nov. 5, 1979, Columbus, Ohio, Abs. No. 157440v Rec. trav.chim. 43, 297, 420 (1924); 71, 814 (1952).

Primary Examiner—Michael G. Wityshyn
Assistant Examiner—Everett White
Attorney, Agent, or Firm—Wayne C. Jaeschke; John E. Drach; Daniel S. Ortiz

[57] ABSTRACT

Alkyl and/or alkenyl oligoglycosides can be obtained in short reaction times and high yields by a process in which glycose is reacted with fatty alcohols at elevated temperature in the presence of sulfomonocarboxylic acids containing 2 to 8 carbon atoms, carboxylic anhydrides thereof and/or mixed cyclic sulfonic/carboxylic anhydrides thereof as acidic catalysts, the water of reaction is removed and the reaction products are worked up.

5 Claims, No Drawings

PROCESS FOR THE PRODUCTION OF ALKYL AND/OR ALKENYL OLIGOGLYCOSIDES

BACKGROUND OF THE INVENTION

1. Field of the Invention

This invention relates to a process for the production of alkyl and/or alkenyl oligoglycosides by acetalization of glycoses with fatty alcohols at elevated temperature in the presence of sulfomonocarboxylic acids as acidic catalysts, removal of the water of reaction and subsequent working up.

2. Statement of Related Art

Surface-active alkyl oligoglycosides, more particularly alkyl oligoglucosides, have long been known as valuable raw materials for the production of detergents and cosmetic products. They are normally produced either by direct acetalization of glycose with fatty alcohols ("direct synthesis") or via the intermediate stage of butyl glycosides which are subjected to transacetalization with fatty alcohols ("butanol route"), the water of reaction and any butanol being continuously removed from the reaction equilibrium. Working up of the crude alkyl oligoglycosides comprises neutralization of the products, removal of the excess fatty alcohol and, optionally, bleaching and conversion into paste form. EP 0 319 616 A1 and WO 90/03977 are cited as representative of the extensive prior art available.

The acetalization of glycoses or the transacetalization of glycosides with fatty alcohols always takes place in the presence of acidic catalysts. Typical examples of such catalysts are sulfuric acid [U.S. Pat. No. 3,974,138], alkyl benzenesulfonic acid [U.S. Pat. No. 5,003,057], p-toluenesulfonic acid [EP 0 301 298 A1] or sulfosuccinic acid [EP 0 415 192 ].

However, the use of the above-mentioned catalysts involves technical difficulties. Where sulfuric acid is used, partial carbonization of the glycose can occur; alkyl benzenesulfonic acid shows unsatisfactory catalytic activity; the use of p-toluenesulfonic acid results in incomplete yields and sulfosuccinic acid is not satisfactorily biodegradable.

Accordingly, the problem addressed by the present invention was to provide new catalysts for the acetalization of glycoses and for the transacetalization of glycosides with fatty alcohols which would be free from the disadvantages mentioned above.

DESCRIPTION OF THE INVENTION

The present invention relates to a process for the production of alkyl and/or alkenyl oligoglycosides by acetalization of glycose with fatty alcohols at elevated temperature in the presence of acidic catalysts, removal of the water of reaction and working up of the reaction mixture, characterized in that the reaction is carried out in the presence of sulfomonocarboxylic acids containing 2 to 8 carbon atoms, carboxylic anhydrides thereof and/or mixed cyclic carboxylic/sulfonic anhydrides thereof as acidic catalysts.

It has surprisingly been found that the use of sulfomonocarboxylic acids in the acetalization reaction leads not only to high yields and small quantities of unwanted secondary products, more particularly polyglycose, but also to short reaction times and, hence, to advantageous utilization of existing plant capacity. In addition, the sulfocarboxylic acids may readily be incorporated in fatty alcohols and, hence, are easy to dose. Finally, the catalysts are distinguished by high ecological and toxicologial compatibility.

Sulfomonocarboxylic acids are known substances which may be obtained by the relevant methods of preparative organic chemistry. In one known method, for example, short-chain hydroxycarboxylic acids are sulfated and then reacted with bisulfite. In addition, short-chain aliphatic carboxylic acids or benzoic acid may be initially introduced in inert solvents and sulfonated with sulfuric acid, chlorosulfonic acid or sulfur trioxide [Rec. trav. chim. 43, 297, 420 (1924); 71, 814 (1952)].

Sulfomonocarboxylic acids suitable as catalysts in accordance with the invention contain 2 to 8 and preferably 2 to 4 carbon atoms. Typical examples are sulfoacetic acid, sulfopropionic acid, sulfobutyric acid, sulfovaleric acid, sulfocaproic acid, sulfocaprylic acid, sulfocapric acid or sulfobenzoic acid. The sulfomonocarboxylic acids may also be used in the form of their carboxylic anhydrides or mixed cyclic sulfonic/carboxylic anhydrides. Examples of such anhydrides are sulfoacetic anhydride and the mixed cyclic sulfonic/carboxylic anhydride of sulfopropionic acid.

The acidic catalysts may be used in quantities of 0.01 to 2% by weight and preferably in quantities of 0.1 to 0.5% by weight, based on the glycose.

Glycoses suitable as starting materials for the production of alkyl and/or alkenyl oligoglycosides by the process according to the invention are aldoses and also ketoses in the broadest sense. Typical examples are glucose, fructose, mannose, galactose, talose, gulose, allose, altrose, idose, arabinose, xylose, lyxose and ribose. Aldoses are preferably used by virtue of their greater reactivity. Among the aldoses, glucose is particularly suitable by virtue of its ready accessibility and availability in commercial quantities. The alkyl and/or alkenyl oligoglycosides most preferably produced by the process according to the invention are therefore the alkyl and/or alkenyl oligoglucosides.

Commercial glucose generally contains 1 mol water of crystallization. This glucose containing water of crystallization may readily be used. However, it has proved to be useful additionally to remove the water of crystallization from the reaction medium by thermal measures before contacting with the catalyst. However, since anhydrous glucose is commercially available in large quantities, it is preferably used in the form of a fine-particle powder.

In the context of the invention, fatty alcohols are primary aliphatic alcohols corresponding to formula (I)

$$R^1\text{—OH} \qquad (I)$$

in which $R^1$ is a linear or branched $C_{4-22}$ alkyl or alkenyl radical.

Typical examples are n-butanol, i-butanol, caproic alcohol, caprylic alcohol, capric alcohol, myristyl alcohol, lauryl alcohol, cetyl alcohol, stearyl alcohol, oleyl alcohol, elaidyl alcohol, petroselinyl alcohol, arachyl alcohol, behenyl alcohol and erucyl alcohol and mixtures thereof.

As is normally the case in oleochemistry, the fatty alcohols may also be present in the form of technical mixtures, for example of the type obtained by high-pressure hydrogenation of methyl esters based on vegetable or animal oils and fats,. for example palm oil, palm kernel oil, coconut oil, rapeseed oil, sunflower oil or beef tallow. Another group of suitable primary alcohols are oxoalcohols in the same C-chain length range which are obtained by hydrogenation of aldehydes from Roelen's oxo reaction and which may contain 5 to 25% by weight branched species. It is preferred to use technical coconut oil fatty alcohol cuts containing 12 to 18 and preferably 12 to 14 carbon atoms.

The molar ratio of glycose to fatty alcohol may be 1:1.5 to 1:10 and is preferably 1:3 to 1:5.

The sulfomonocarboxylic acids may be contacted with the glycose and the fatty alcohol while stirring. It is not critical whether mixing takes place before heating or whether the catalyst is added to the mixture of glycose and fatty alcohol heated to the reaction temperature. In one preferred embodiment of the process according to the invention, the sulfomonocarboxylic acids are preformed in part of the fatty alcohol, i.e. dissolved with stirring at temperatures of 20° to 40° C., and subsequently added to the reaction mixture of glycose and residual fatty alcohol at the reaction temperature. In some cases, however, particularly in the production of short-chain alkyl and/or alkenyl glycosides, it can also be of advantage for the fatty alcohol initially introduced and the solvent for the acidic catalyst to be different. Both embodiments have proved to be optimal in regard to ready solubility of the catalyst in the reaction mixture.

The actual acetalization reaction may take place at temperatures of 80° to 130° C. and preferably at temperatures of 90° to 120° C. It has proved to be of advantage to carry out the reaction under a reduced pressure of 1 to 100 mbar.

In addition, to displace the equilibrium, it is advisable continuously to remove the water of reaction formed and any water introduced with the starting materials, for example using a distillation column. Where short-chain fatty alcohols which readily form volatile azeotropes with water are used, it is advisable to work up the aqueous alcohols after distillation and to return the valuable product.

The reaction is over when no more water of reaction is formed and distilled off. To ensure that substantially all the glycose, i.e. at least 99% by weight, based on the starting quantity, has reacted, it is advisable to subject the reaction mixture to an after-reaction at the reaction temperature and to check the residual sugar content, for example by the FEHLING test.

Further working up of the crude alkyl and/or alkenyl oligoglycosides may be carried out by methods known per se. The acidic reaction products are first neutralized with alkali metal and/or alkaline earth metal oxides, hydroxides or carbonates and the excess fatty alcohol is subsequently removed by distillation, preferably using a thin-layer evaporator, at a temperature of 160° to 240° C. and under a reduced pressure of 1 to 10 mbar. In most cases, it is advisable to subject the resulting alkyl and/or alkenyl oligoglycosides to bleaching and, optionally, to convert them into paste form with water at the same time.

Industrial Applications

The alkyl and/or alkenyl oligoglycosides produced by the process according to the invention are distinguished by a low polyglycose content and have surface-active properties. Accordingly, they are suitable for the production of laundry detergents, dishwashing detergents and cleaning preparations and also hair-care and body-care products in which they may be present in quantities of 0.1 to 50% by weight and preferably in quantities of 1 to 25% by weight, based on the particular preparation.

The following Examples are intended to illustrate the invention without limiting it in any way.

Examples

General procedure 180 g (1 mol) anhydrous glucose and 870 g (4.5 mol) $C_{12/14}$ coconut oil fatty alcohol (Lorol® S, hydroxyl value 290, Henkel KGaA, Düsseldorf, Germany) were introduced into a 2 liter three-necked flask equipped with a stirrer, distillation column and internal thermometer and heated to 110° C. under a reduced pressure of approximately 20 mbar. 0.1 to 0.5% by weight, based on the glucose, of catalyst in the form of a 5% by weight solution in coconut oil fatty alcohol was then added to the reaction mixture. To displace the equilibrium, the water of reaction was continuously distilled off and the reaction was terminated after the elimination of water had stopped and the residual content of unreacted glucose in the mixture was less than 1% by weight, based on the starting quantity. The reaction mixture was then neutralized with magnesium oxide and the excess coconut oil fatty alcohol was removed under reduced pressure (approx. 1 mbar) and at a temperature of 180° C. using a thin-layer evaporator.

Particulars of the test mixtures and the characteristic data of the products are set out in Table 1.

TABLE 1

| | | | | | | |
|---|---|---|---|---|---|---|
| Acetalization of glucose with coconut oil fatty alcohol percentages in % by weight | | | | | | |
| Example | Cat. | c(Cat) % | t min. | Y g | c(Pol) % | ADP |
| 1 | A1 | 0.1 | 390 | 288 | 5.2 | 1.37 |
| 2 | A2 | 0.1 | 330 | 285 | 5.5 | 1.34 |
| C1 | B | 0.1 | 900 | 286 | 5.7 | 1.33 |
| C2 | B | 0.5 | 420 | 286 | 6.1 | 1.33 |

Legend:
Cat. = catalyst
c(Cat) = catalyst concentration
t = reaction time
Y = yield
c(Pol) = polyglucose content
ADP = average degree of polymerization
A1 = sulfoacetic acid
A2 = mixed cyclic sulfonic/carboxylic anhydride of sulfopropionic acid
B = dodecyl benzenesulfonic acid

What is claimed is:

1. A process for making an alkyl or alkenyl oligoglycoside which comprises reacting glycose with a fatty alcohol in the presence of an acid catalyst selected from the group consisting of sulfomonocarboxylic acids having from 2 to 8 carbon atoms, anhydrides of sulfomonocarboxylic acids having from 2 to 8 carbon atoms, mixed cyclic sulfonic acid carboxylic acid anhydrides, and mixtures thereof.

2. The process of claim 1 wherein said sulfomonocarboxylic acid is selected from the group consisting of sulfoacetic acid, sulfopropionic acid, sulfobutyric acid, sulfobenzoic acid, and combinations thereof.

3. The process of claim 1 wherein said acid catalyst is present in an amount equal to from about 0.01% to about 2.0% by weight of said glycose.

4. The process of claim 1 wherein said glycose is glucose.

5. The process of claim 1 wherein said fatty alcohol is a compound of the formula I $$R^1\text{—OH} \qquad (I)$$

wherein $R^1$ is a linear or branched alkyl or alkenyl radical having from 4 to about 22 carbon atoms.